(12) United States Patent
Lu et al.

(10) Patent No.: US 9,937,254 B2
(45) Date of Patent: *Apr. 10, 2018

(54) WATER-SOLUBLE SUPRAMOLECULAR COMPLEXES

(71) Applicant: Broda Technologies Co., Ltd., Shanghai (CN)

(72) Inventors: Shao Xiang Lu, Plainsboro, NJ (US); Jeffrey Lu, Plainsboro, NJ (US); Letian Liu, Plainsboro, NJ (US)

(73) Assignee: Broda Technologies Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,835

(22) Filed: Jan. 17, 2017

(65) Prior Publication Data

US 2017/0128574 A1 May 11, 2017

Related U.S. Application Data

(60) Continuation-in-part of application No. 14/548,851, filed on Nov. 20, 2014, now abandoned, and a continuation-in-part of application No. 15/054,427, filed on Feb. 26, 2016, now Pat. No. 9,592,295, which is a continuation of application No. 14/492,288, filed on Sep. 22, 2014, now abandoned, which is a division of application No. 13/425,923, filed on Mar. 21, 2012, now Pat. No. 8,865,143, which is a continuation of application No. PCT/CN2011/000462, filed on Mar. 21, 2011.

(51) Int. Cl.
| | | |
|---|---|---|
| A61K 47/10 | (2017.01) | |
| A61K 31/137 | (2006.01) | |
| A61K 31/60 | (2006.01) | |
| A61Q 19/08 | (2006.01) | |
| A61K 8/86 | (2006.01) | |
| A61K 8/33 | (2006.01) | |
| A61K 8/368 | (2006.01) | |
| A61Q 5/00 | (2006.01) | |

(52) U.S. Cl.
CPC ............ *A61K 47/10* (2013.01); *A61K 8/33* (2013.01); *A61K 8/368* (2013.01); *A61K 8/86* (2013.01); *A61K 31/137* (2013.01); *A61K 31/60* (2013.01); *A61Q 5/006* (2013.01); *A61Q 19/08* (2013.01); *A61K 2800/262* (2013.01)

(58) Field of Classification Search
CPC ...... A61K 47/10; A61K 8/368; A61K 31/137; A61K 2800/262; A61Q 5/006
See application file for complete search history.

(56) References Cited

U.S. PATENT DOCUMENTS

| | | |
|---|---|---|
| 4,188,373 A | 2/1980 | Krezanoski |
| 4,474,751 A | 10/1984 | Haslam |
| 4,478,822 A | 10/1984 | Haslam et al. |
| 4,810,503 A | 11/1989 | Carson et al. |
| 5,187,191 A | 2/1993 | Otten et al. |
| 5,208,031 A | 5/1993 | Kelly |
| 5,252,318 A | 10/1993 | Joshi et al. |
| 5,256,396 A | 10/1993 | Piechota |
| 5,266,321 A | 11/1993 | Shukuzaki et al. |
| 5,298,260 A | 3/1994 | Viegas |
| 5,538,793 A | 7/1996 | Inokuchi et al. |
| 5,593,683 A | 1/1997 | Viegas et al. |
| 5,629,260 A | 5/1997 | Utz et al. |
| 6,316,011 B1 | 11/2001 | Ron et al. |
| 6,713,093 B2 | 3/2004 | Takahata et al. |
| 8,865,143 B2 | 10/2014 | Lu et al. |
| 2004/0158941 A1 | 8/2004 | Geary et al. |
| 2005/0220831 A1* | 10/2005 | Jorsal ............... A61K 8/068 424/401 |
| 2007/0211212 A1 | 9/2007 | Bennwik |
| 2009/0196942 A1 | 8/2009 | Goyarts et al. |
| 2009/0325938 A1 | 12/2009 | Lichter et al. |

(Continued)

FOREIGN PATENT DOCUMENTS

| | | |
|---|---|---|
| CN | 1753949 A | 3/2006 |
| CN | 1869128 A | 11/2006 |

(Continued)

OTHER PUBLICATIONS

2006 BASF Technical Bulletin entitled "Pluronic® F127 surfactant viscosity as a function of temperature & concentration"—1 page.

(Continued)

*Primary Examiner* — Jianfeng Song
(74) *Attorney, Agent, or Firm* — RatnerPrestia

(57) ABSTRACT

Water-soluble supramolecular complexes formed from a water soluble block copolymer and at least one associative gelling adjuvant. The copolymer includes at least two blocks of polyethylene oxide and at least one block of polypropylene oxide. The adjuvant has a water solubility less than 0.5 g/100 ml at 20° C. When combined with water, the complexes form a transparent reversely thermo-reversible hydrogel or solution that may be repeatedly hydrated and dehydrated. The hydrogel exhibits improved gelling efficiency and enhanced solubility and/or stability for sparely soluble and insoluble pharmaceutical agents. The complexes are useful in a variety of pharmaceutical and cosmetic products and applications and may be combined with an effective amount of a cosmetic, medicament, or diagnostic in a solid dosage form.

25 Claims, No Drawings

(56) References Cited

U.S. PATENT DOCUMENTS

| | | | |
|---|---|---|---|
| 2010/0105801 A1* | 4/2010 | Choi | A61L 27/16 523/115 |
| 2010/0150850 A1 | 6/2010 | Tamor | |
| 2012/0244097 A1 | 9/2012 | Lu et al. | |

FOREIGN PATENT DOCUMENTS

| | | |
|---|---|---|
| CN | 101536974 A | 9/2009 |
| EP | 2689774 A1 | 1/2014 |
| GB | 1207438 | 7/1968 |
| JP | 04225914 | 8/1992 |
| JP | 11222419 | 8/1999 |
| JP | 2006519272 A | 8/2006 |
| JP | 2010520943 A | 6/2010 |
| WO | 2004076561 A1 | 9/2004 |
| WO | 2009055312 A1 | 4/2009 |
| WO | 2010006376 A1 | 1/2010 |

OTHER PUBLICATIONS

BASF The Chemical Company, "Lutrol® L and Lutrol® F-Grades", Apr. 2010, pp. 1-8.

Decision to Grant dated Jul. 19, 2016 for Japanese Application No. 2014-500219, including translation, 6 pages.

Extended European Search Report dated Jul. 16, 2014 in counterpart European Application No. 11861767.9-1460—6 pages.

European Office Action for European Aplication No. 11 861 767.9-1460, dated Apr. 12, 2016—5 pages.

Final Office Action dated Jul. 14, 2016 for U.S. Appl. No. 14/548,851—12 pages.

The HLB System A Time-Saving Guide to Emulsifier Selection, © 1976 ICI Americas, Inc. pp. 1-22.

The HLB System A Time-Saving Guide to Surfactant Selection, Uniqema Presentation, Mar. 9, 2004—39 pages.

International Search Report for International Application No. PCT/US2015/061553, dated Feb. 12, 2016—13 pages.

International Search Report PCT/CN2011/000462, dated Dec. 8, 2011—1 page.

Japanese Office Action dated Aug. 26, 2014 in corresponding Japanese Patent Application No. 2014/500219—8 pages.

Lehn, Agnew. Chem. Int. Ed. Engl., vol. 29, pp. 1304-1319 (1990).

Materials Safety Data Sheet, SupraSalix-16, Brodatech, Materials Safety Data Sheet, Sep. 23, 2014, 2 pages.

U.S. Notice of Allowance for U.S. Appl. No. 15/054,427, dated Nov. 11, 2016—24 pages.

Office Action in U.S. Appl. No. 14/548,851, dated Mar. 30, 2016—24 pages.

Office Action in U.S. Appl. No. 14/492,288, dated Aug. 12, 2015—18 pages.

Office Action in U.S. Appl. No. 14/492,288, dated Nov. 27, 2015—16 pages.

"SupraSalix-16," Brodatech, Product Specifications, Sep. 30, 2014, 1 page.

"SupraSalix-16," Brodatech, Technical Data Sheet, 1 page, 2014.

Entire patent prosecution history of U.S. Appl. No. 13/425,923, filed Mar. 21, 2012, entitled "Reversely Thermo-Reversible Hydrogel Compositions," now U.S. Pat. No. 8,865,143, issued Oct. 21, 2014.

Entire patent prosecution history of U.S. Appl. No. 14/548,851, filed Nov. 20, 2014, entitled Water-Soluble Supramolecular Complexes.

Entire patent prosecution history of U.S. Appl. No. 14/492,288, filed Sep. 22, 2014, entitled Reversely Thermo-Reversable Hydrogel Complexes.

* cited by examiner

WATER-SOLUBLE SUPRAMOLECULAR COMPLEXES

This application is a continuation-in-part of U.S. application Ser. No. 14/548,851, filed Nov. 20, 2014. This application is also a continuation-in-part of U.S. application Ser. No. 15/054,427, filed Feb. 26, 2016, which is a continuation of U.S. application Ser. No. 14/492,288, filed Sep. 22, 2014, which is a divisional of U.S. application Ser. No. 13/425,923, filed Mar. 21, 2012, now U.S. Pat. No. 8,865,143 issued Oct. 21, 2014, which is a continuation of PCT/CN2011/000462, filed Mar. 21, 2011.

FIELD OF THE INVENTION

The present invention relates to water-soluble supramolecular complexes for the delivery of pharmaceutical agents or cosmetics active ingredients, specifically water-soluble supramolecular complexes in the form of solids that when hydrated are able to form transparent hydrogels or solutions.

BACKGROUND

The field of applying active ingredients to humans and animals is, of course, wide ranging and comprises for example, the delivery and application of active ingredients for pharmaceutical and cosmetic purposes. It is specifically desirable to provide such compositions that are capable of solubilizing and stabilizing water insoluble or sparely soluble active ingredients in water.

Supramolecular Chemistry has expanded the scope of Chemistry allowing for the design and development of smart and functional materials. While traditional synthetic molecules are covalently-linked molecules or macromolecules, supramolecular complexes contain non-covalent binding on the association of two or more building blocks which are held together by intermolecular bonds, such as hydrogen bonding, dipole-dipole interactions, van der Waals forces, cation-pi interactions, pi-pi bonds, CH/pi interactions, or hydrophobic effects, and etc. showing inclusion, selectivity and other functionality.

Reversely thermo-reversible gelling systems are known in which the solution viscosity increases and decreases with an increase and decrease in temperature, respectively. Such system exhibits a solution to gel (sol-gel) transition which transforms a low viscosity solution to a higher viscosity gel form as the temperature increases, with continued increases in temperature, the gelled system then experiences a gel to solution (gel-sol) transition which transforms the gelled system back to a liquid solution. Such reversely thermo-reversible gelling systems are useful wherever it is desirable to handle a composition in a liquid state, and/or the performance of the composition in a gel form.

A known material with these properties is a reversely thermo-reversible hydrogel using water soluble block copolymers of polyethylene oxide and polypropylene oxide available commercially as Pluronic® from BASF (Ludwigshafen, Germany) and generically known as Poloxamers. Generally, about 20% w/w Pluronic® F127 aqueous solution is liquid when at or below about 25° C. or heated to temperatures exceeding 70° C., but turns into gel form and exhibits maximum viscosity in the range of 30-60° C. (see 2006 BASF Technical Bulletin entitled "Pluronic® F127 surfactant viscosity as a function of temperature & concentration"; and April 2010 "Lutrol® L and Lutrol® F-Grades"). Typically, concentrations of Pluronic® F127 polymer of at least 18-20% by weight are needed to produce a sol-gel transition temperature at about 25° C., room temperature range. To decrease the desired sol-gel transition temperature further below 25° C., a higher concentration of Poloxamer polymer has to be used which in turn increases the viscosity of solution and results in unfavorable physiological interaction during use. The freedom to use Poloxamer polymers with adjustable sol-gel transition temperatures, specifically, at temperatures below about 25° C. without employing higher concentrations of polymer, is limited.

U.S. Pat. Nos. 4,188,373, 4,478,822 and 4,474,751 disclose the use of nonionic block copolymers of polyethylene oxide and polypropylene oxide Poloxamers in aqueous pharmaceutical compositions. In these systems, the concentration of polymer is adjusted to give the desired sol-gel transition temperature. However, concentrations of the poloxamer polymer of at least 18-20% by weight are needed to produce a composition which exhibits such a transition at commercially or physiologically useful temperatures. Also, solutions containing more than 18-20% by weight of block copolymer at the desired sol-gel transition temperature are typically very viscous even in the "liquid" state. In addition, the high polymer concentrations may cause unfavorable physiological interactions with target tissue during use.

U.S. Pat. No. 5,256,396 to Piechota et al. discloses an oral composition of a water dispersible active ingredient with the use of Pluronic F127. These compositions are flowable liquids below 82° F. (27.8° C.), and gels when heated to 82° F. (27.8° C.).

U.S. Pat. No. 5,252,318 to Joshi et al. discloses reversible gelling compositions which comprise a blend of a pH-sensitive gelling polymer and a thermo-sensitive gelling polymer, such as Pluronic F 127. The sol-gel transition temperature adjustment has been achieved at relatively low Pluronic F127 polymer concentrations upon simultaneous change in temperature and pH.

U.S. Pat. No. 6,316,011 to Ron et al. discloses a reversely thermo-sensitive gelling composition comprising an end-modified block copolymer of polyethylene oxide and polypropylene oxide, the composition reversibly gelling at a temperature in the range of 22° C. to 40° C.

The references cited above are generally concerned with reversely thermo-reversible hydrogel compositions which are in a liquid state at room temperature or below, subsequently transform to a gel form when warmed to body temperature after application, and have to employ a high concentration of polymer. However, for many pharmaceutical and cosmetic products and applications, a gel form hydrogel composition is more preferred under use conditions, i.e. in the form of a gel at room temperature. In addition, the liquid state of such systems at room temperature presents a lot of challenges in regard to the solubility and/or stability of sparely soluble or insoluble active ingredients in such aqueous liquid solutions. For example, the use of salicylic acid or its derivatives for treating dandruff, acne, skin wrinkling, skin pigmentation, warts, freckles, or skin-related problems is well known in the preparation of dermatologic and cosmetic formulations. Salicylic acid and its derivatives are usually in crystalline form and are not sufficiently soluble in water or oils traditionally used in dermatological and cosmetic preparations. Typical problems that occur when using salicylic acid or its derivatives in making dermatologic and cosmetic products are that the salicylic acid and its derivatives tend to crystallize out within various compositions, which significantly reduces the bioavailability of salicylic acid and its derivatives for treating or preventing the aforementioned skin problems. Further, salicylic acid and its derivatives provide formulations that form crystals on standing and precipitate out within the solution, which is unpleasant with regard to texture and appearance from the consumer's viewpoint.

U.S. Pat. No. 8,865,143 to Lu et al. discloses reversely thermo-reversible hydrogel compositions comprising water soluble block copolymers of polyethylene oxide and polypropylene oxide and at least one associative gelling adjuvant in a temperature range of 4-45° C. The hydrogel compositions disclosed in this reference have substantial water weight, which make shipping and handling difficult and expensive, and it is not known from this reference how to overcome this disadvantage.

Accordingly, there remains a need for improved delivery compositions comprising water soluble block copolymers of polyethylene oxide and polypropylene oxide for solubilizing water insoluble or sparely soluble active ingredients, particularly reversely thermo-reversible hydrogel or solution compositions comprising such block copolymers of polyethylene oxide and polypropylene oxide, which have extended gel form under use conditions, specifically at below room temperature, and have acceptable or improved solubility and/or stability for sparely soluble or insoluble active ingredients at relatively low polymer concentration, useful for pharmaceutical and cosmetic products and applications.

SUMMARY

According to one embodiment of the present invention, a composition is provided that comprises water-soluble supramolecular complexes that when hydrated are able to form a reversely thermo-reversible hydrogel composition that possesses bioadhesive or mucoadhesive properties or a solution. In one exemplary embodiment, the complexes are provided as a solid, wax-like material, a gel, or a solution that is capable of gelling upon contact with dermal or mucosal tissue.

In another exemplary embodiment, the present invention provides a composition comprising water-soluble supramolecular complexes that include:
  (a) a water soluble block copolymer comprising at least two blocks of polyethylene oxide and at least one block of polypropylene oxide, wherein the copolymer is selected from the group consisting of:
    (i) a tri-block copolymer having the general formula of $HO\text{-}(EO)_a(PO)_b(EO)_a\text{---}H$, wherein $50 \leq a \leq 150$ and $35 \leq b \leq 70$;
    (ii) a linear multi-block copolymer, having the general formula of $HO\text{---}[(PO)_b(EO)_a]_m(PO)_c[(EO)_a(PO)_b]_m\text{---}H$, wherein $50 \leq a \leq 150$, $35 \leq b \leq 70$, $35 \leq c \leq 70$, and $m>0$;
    (iii) a chain extended, hyper-branched, or star-shaped block copolymer of the formula $\{[A_n(EO)_a(PO)(EO)_aA_n]E\}_m$, wherein A is a monomer selected from the group consisting of esters, hydroxyl acid esters, carbonates, ethers, siloxanes, and amides, and E is a chain extender or crosslinking agent, $50 \leq a \leq 150$, $35 \leq b \leq 70$, $0 \leq n \leq 50$, and $m \geq 2$;
    (iv) an end-modified block copolymer of the formula $R\text{-}G\text{-}(EO)_a(PO)_b(EO)_a\text{-}G\text{-}R$, wherein G is selected from the group consisting of C—C, C—O, C(O)NH, S—C, C(O)—O, or Si—O, R is alkyl or arylalkyl having an alkyl chain length in the range of $C_8$-$C_{36}$, $50 \leq a \leq 150$, $35 \leq b \leq 70$; and
    (v) a grafted block copolymer, comprising a grafted side chain, comprising at least two blocks of polyethylene oxide, and at least one block of polypropylene oxide, and having the formula $[A(EO)_a(PO)_b(EO)_a]_m$, $50 \leq a \leq 150$, $50 \leq b \leq 150$, A is selected from the group consisting of vinyl, ester, amide, imide, ether, and siloxane linkages, $m \geq 2$;
  wherein (EO) is a polyethylene oxide block and (PO) is a polypropylene oxide block; and
  (b) at least one associative gelling adjuvant having a water solubility less than 0.5 g/100 ml at 20° C.;
wherein the complexes are capable of being repeatedly hydrated and dehydrated with water to form a solution or a transparent reversely thermo-reversible hydrogel, and wherein the composition is provided in solid form. The solution or the transparent reversely thermo-reversible hydrogel may form in a temperature range of 4-45° C. Also, the transparent reversely thermo-reversible hydrogel may have an adjustable sol-gel transition temperature in a temperature range from about 4-40° C.

In yet another exemplary embodiment, the present invention provides a composition consisting essentially of:
  (a) a water soluble block copolymer comprising at least two blocks of polyethylene oxide and at least one block of polypropylene oxide, wherein the copolymer is selected from the group consisting of:
    (1) a tri-block copolymer having the general formula of $HO\text{-}(EO)_a(PO)_b(EO)_a\text{---}H$, wherein $50 \leq a \leq 150$ and $35 \leq b \leq 70$;
    (2) a linear multi-block copolymer, having the general formula of $HO\text{---}[(PO)_b(EO)_a]_m(PO)_c[(EO)_a(PO)_b]_m\text{---}H$, wherein $50 \leq a \leq 150$, $35 \leq b \leq 70$, $35 \leq c \leq 70$, and $m>0$;
    (3) a chain extended, hyper-branched, or star-shaped block copolymer of the formula $\{[A_n(EO)_a(PO)_b(EO)_aA_n]E\}_m$, wherein A is a monomer selected from the group consisting of esters, hydroxyl acid esters, carbonates, ethers, siloxanes, and amides, and E is a chain extender or crosslinking agent, $50 \leq a \leq 150$, $35 \leq b \leq 70$, $0 \leq n \leq 50$, and $m \geq 2$;
    (4) an end-modified block copolymer of the formula $R\text{-}G\text{-}(EO)_a(PO)_b(EO)_a\text{-}G\text{-}R$, wherein G is selected from the group consisting of C—C, C—O, C(O)NH, S—C, C(O)—O, or Si—O, R is alkyl or arylalkyl having an alkyl chain length in the range of $C_8$-$C_{36}$, $50 \leq a \leq 150$, $35 \leq b \leq 70$;
    (5) a grafted block copolymer, comprising a grafted side chain, comprising at least two blocks of polyethylene oxide, and at least one block of polypropylene oxide, and having the formula $[A(EO)_a(PO)_b(EO)_a]_m$, $50 \leq a \leq 150$, $50 \leq b \leq 150$, A is selected from the group consisting of vinyl, ester, amide, imide, ether, and siloxane linkages, $m \geq 2$;
  wherein (EO) is a polyethylene oxide block and (PO) is a polypropylene oxide block; and
  (b) at least one associative gelling adjuvant having a water solubility less than 0.5 g/100 ml at 20° C.;
wherein the water soluble block copolymer and the at least one associative gelling adjuvant form water-soluble supramolecular complexes, the water-soluble supramolecular complexes are capable of being repeatedly hydrated and dehydrated to form at least one of an aqueous solution and a transparent reversely thermo-reversible hydrogel, and wherein the composition is provided in solid form. The use of "consisting essentially of" means that additional additives are not required to solubilize either the associative gelling adjuvant or an active ingredient in the composition according to the invention.

According to another embodiment of the present invention, a wet method of forming a composition comprising water-soluble supramolecular complexes includes dissolving a water soluble block copolymer in water at a temperature below 20° C., mixing the dissolved copolymer with at least one associative gelling adjuvant at a suitable temperature to form a transparent hydrogel or solution, and drying the transparent hydrogel or solution until at least 45% of the water is removed from the transparent hydrogel or solution to provide the solid form.

According to yet another embodiment of the present invention, a hot melt processing method of forming a composition comprising water-soluble supramolecular complexes includes heating the water soluble block copolymer to a temperature of 55 to 120° C., mixing the heated copolymer with at least one associative gelling adjuvant at a temperature of 55 to 120° C. to form a mixture, and cooling the mixture.

As used herein, "at least one", "one or more", and "and/or" are open-ended expressions that are both conjunctive and disjunctive in operation. It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

DETAILED DESCRIPTION

The present invention provides, in one embodiment, water-soluble supramolecular complexes comprising a water soluble block copolymer that includes at least two blocks of polyethylene oxide and at least one block of polypropylene oxide, and at least one associative gelling adjuvant, having a water solubility of less than 0.5 g/100 ml, preferably less than 0.3 g/100 ml, more preferably less than 0.1 g/100 ml at 20° C., and being capable of forming a reversely thermo reversible hydrogel when the complexes are combined with water. The reversely thermo-reversible hydrogel may have an adjustable sol-gel transition temperature in the range of from about 4-45° C., preferably from about 8-40° C., and serve as a vehicle for a cosmetic active ingredient or an effective amount of at least one pharmaceutical medicament.

While not wishing to be bound by any particular theory it is proposed herein that the inter-molecular interactions, such as hydrogen bonding interaction, between the associative gelling adjuvant and the water soluble block copolymer, comprising at least two blocks of polyethylene oxide and at least one block of polypropylene oxide, result in the formation of the water-soluble supramolecular complexes, which are responsible for the observation of enhanced gelling efficiency of the compositions and further enhanced solubility and/or stability of water insoluble or sparely soluble drugs made according to the present invention.

"Water-soluble supramolecular complexes" as used herein and in the appended claims means a molecular self-assembly where two or more compounds interact with each other via various weak intermolecular interactions, such as, for example, hydrogen bonding, dipole-dipole interactions, van der Waals forces, cation-pi interactions, pi-pi bonds, CH/pi interactions, or hydrophobic effects, resulting in the formation of intermolecular complexes with enhanced or different functionality comparing with each individual molecules, such as water solubility.

According to various embodiments of the present invention, it has been found that anhydrous water-soluble supramolecular complexes or complexes having low water content may be hydrated to form a transparent hydrogel or solution, i.e. a single phase hydrogel or liquid, depending on the concentration of the preparation. The temperature or solid content of the resulting preparations may then be increased or decreased to form a reversely thermo-reversible gel or solution that is transparent and capable of solubilizing active ingredients that are generally insoluble in water. It has been found that a reversely thermo-reversible gel or solution containing the water-soluble supramolecular complexes according to the present invention may be repeatedly dehydrated and rehydrated without the loss of their soluble functionality or other advantageous properties. The ratio of the water soluble block copolymer to the at least one associative gelling adjuvant within the various compositions of the present invention may be 0.5:1 to 15:1, more preferably 1:1 to 10:1, and most preferably 2:1 to 5:1.

Compositions according to the present invention may contain water-soluble supramolecular complexes and have a low water content, preferably less than 55 wt. %, more preferably less than 25 wt. %, and most preferably less than 5 wt. % of water relative to the total weight of the complexes. The compositions having low to no water content may be provided in the form of a waxy solid or paste. The waxy material exhibits a softening point ranging from 10 to 60° C.

Compositions according to an embodiment of the present invention may consist essentially of a water soluble block copolymer and an associative gelling adjuvant, as well as optionally, an active ingredient. Additional solvents or additives are not required to increase the water solubility of the active ingredient associated with the water soluble block copolymer and associative gelling adjuvant that may form water-soluble supramolecular complexes.

As used herein and in the appended claims, the term "gel" in reference to the present hydrogel compositions, means that the composition is a solid, jelly-like material that can have properties ranging from soft and weak to hard and tough. Gels are dilute systems, which exhibit no flow when in the steady-state.

As used herein and in the appended claims, the term "reversely thermo-reversible" in reference to the present hydrogel compositions, means that the process of gelation takes place upon an increase in temperature rather than a decrease in temperature. This is counter-intuitive because solution viscosity typically decreases with an increase in temperature.

Sol-gel or gel-sol transition temperature may be measured by visually determining the gel melting temperature by the vial inversion method. Sample vials were immersed in an inverted position in a water bath and the temperature was decreased or increased slowly. The gel melting temperature was taken as the temperature at which the gel started to flow.

By "use conditions" as that term is used herein, it is meant all conditions to which the complexes or hydrogel compositions are likely to be exposed during use, including during shipment and storage, as well as during medical treatment or personal care.

The terms "pharmaceutically acceptable," "physiologically acceptable," and "cosmetically acceptable" and grammatical variations thereof, as used herein and/or in the appended claims as they refer to electrolytes (e.g., salts), bases, diluents, preservatives, buffers and other excipients, are used interchangeably and mean that the materials are capable of topical administration to human skin, the esophagus, otic, vagina, rectum, or ophthalmus without the unacceptable production of undesirable physiological effects such as irritation, itching, stinging, or systemic effects such as nausea, dizziness, and the like.

The term "leave-on" type product as used herein and/or in the appended claims means a product that is left on the skin upon application. Examples of leave-on products include anti-aging cream, body lotion/cream, deodorants, and hand lotion/cream. The term "rinse-off" type product as used herein and/or in the appended claims means that the product that is rinsed-off shortly after application and use. Rinse-off products are products like shampoo, hair conditioner, and facewash.

All percentages mentioned herein are percentages by weight unless otherwise indicated.

Water Soluble Block Copolymer Comprising at Least Two Blocks of Polyethylene Oxide and at Least One Block of Polypropylene Oxide The terms "polyethylene oxide," "PEO," "EO," "polyethylene glycol," and "PEG" are used interchangeably and refer to synthetic polymers of ethylene oxide represented by the following chemical structure:

(1)

in which a is an integer representing the average number of monomer repeating units.

The terms "polypropylene oxide," "PPO," "PO," "polypropylene glycol," and "PPG" are used interchangeably and refer to synthetic polymers of propylene oxide represented by the following chemical structure:

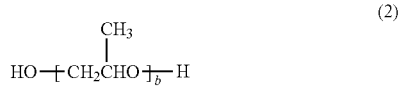

(2)

in which b is an integer representing the average number of monomer repeating units.

A block copolymer of polyethylene oxide and polypropylene oxide refers to a synthetic copolymer of polyethylene oxide (Formula 1) and polypropylene oxide (Formula 2), of varying molecular weights, and of various types, ranging from linear multi-block copolymers, side-chain grafted block copolymers, and hyper-branched block copolymers to star-shaped block copolymers. The block copolymers of polyethylene oxide and polypropylene oxide also comprise end-modified and chain-extended block copolymers of various types.

Water soluble block copolymers that may be incorporated in various embodiments of the present invention are block copolymers comprising at least two blocks of polyethylene oxide of the formula, $-[CH_2CH_2O]_a-$, and at least one block of polypropylene oxide of the formula, $-[CH_2CH(CH_3)O]_b-$, where a and b are each integers in the range of about 10-150, representing the average number of monomer repeating units in the polymer.

Exemplary water soluble block copolymers comprising at least two blocks of polyethylene oxide and at least at least one block of polypropylene oxide that may be used in the present invention are tri-block copolymers commercially available under the trade name PLURONIC®, also known as Poloxamer from BASF Corporation, Mount Olive, N.J. Preferred Poloxamer polymers, having the general formula of $HO-(EO)_a(PO)_b(EO)_a-H$, are PLURONIC® F127 (also known as Poloxamer 407) with average values of a at about 101, and b at about 56, and PLURONIC® F108 (also known as Poloxamer 338) with average values of a at about 141, and b at about 44, respectively.

Other exemplary water soluble block copolymers comprising at least two blocks of polyethylene oxide and at least one block of polypropylene oxide include linear multi-block copolymers, having the general formula of $HO-[(PO)_b(EO)_a]_m(PO)_c[(EO)_a(PO)_b]_m-H$, where $(EO)_a$ is a polyethylene oxide block, and $(PO)_b$ or $(PO)_c$ is a polypropylene oxide block, a, b, and c are each integers in the range of about 10-150, and m is an integer greater than 0.

Other water soluble multi-block copolymers include chain extended, hyper-branded, or star-shaped block copolymers of the formula $\{[A_n(EO)_a(PO)_b(EO)_aA_n]E\}_m$, where $(EO)_a$ is a polyethylene oxide block, and $(PO)_b$ is a polypropylene oxide block, A is a monomer repeating unit, E is a chain extender or crosslinking agent, n is an integer ranging from 0 to 50, preferably 1 to 20 (0 to 20 in the case of non-biodegradable materials), even more preferably 2 to 16 (0 to 16 in the case of non-biodegradable materials), and m is the number of repeating units in the polymer molecule and is an integer equal to or greater than 2 (within practical limits, up to about 100,000 or more), preferably ranging from about 2 to about 500, more preferably about 3 to 100. Thus, where n is 0, the present invention contemplates polymers of the structure $\{[(EO)_a(PO)_b(EO)_a]E\}_m$.

The water soluble block copolymers used in the present invention may also include an end-modified block copolymers of general formula $R-G-(EO)_a(PO)_b(EO)_a-G-R$, where $(EO)_a$ is a polyethylene oxide block, and $(PO)_b$ is a polypropylene oxide block, G is selected from a group consisting of C—C, C—O, C(O)NH, S—C, C(O)—O, and Si—O, R is alkyl or arylalkyl with alkyl chain length in the range of C6-C36, a is an integer ranging from 50 to 150, b is an integer ranging from 35 to 70.

Exemplary end-modified water soluble block copolymers having alkyl or arylalkyl end-modifiers comprise at least two blocks of polyethylene oxide and at least one block of polypropylene oxide, which are a product of alcohol condensation reactions with a terminal alkyl or arylalkyl group. The alkyl group may have hydrophobic character, such as butyl, hexyl and the like. An alkyl poloxamer may have the general formula $R-[(EO)_a(PO)_b(EO)_a]_m-R'$, where $(EO)_a$ is a polyethylene oxide block, $(PO)_b$ is a polypropylene oxide block, R and R' are the nonpolar pendant groups, such as alkyl and arylalkyl with alkyl chain length in the range of C6-C36, and m is an integer ranging from 1-10.

Other exemplary water soluble block copolymers that may be used in the present invention are grafted block copolymers comprising grafted side chains of at least two blocks of polyethylene oxide and at least one block of polypropylene oxide, having general formula of $[A(EO)_a(PO)_b(EO)_a]_m$, where $(EO)_a$ is a polyethylene oxide block, $(PO)_b$ is a polypropylene oxide block, a and b are each integers in the range of about 10-150. "A" may be selected from the group consisting of vinyl, ester, amide, imide, ether, siloxane linkages, and the like, and m is the number of repeating units in the polymer molecule and is an integer equal to or greater than 2.

Water soluble multi-block copolymers that may be used in the present invention include polyester chain extended block copolymers of the formula $\{[A_n(EO)_a(PO)_b(EO)_aA_n]E\}_m$, where $(EO)_a$ is a polyethylene oxide block, $(PO)_b$ is a polypropylene oxide block, A is a monomer repeating unit, (EO)$_a$ is a polyethylene oxide block, and (PO)$_b$ is a polypropylene oxide block as previously defined, E is a chain extender or crosslinking agent, n is an integer ranging from 0 to 50, preferably 1 to 20 (0 to 20 in the case of non-biodegradable materials), even more preferably 2 to 16 (0 to 16 in the case of non-biodegradable materials) and m is the number of repeating units in the polymer molecule and is an integer equal to or greater than 2, preferably ranging from about 2 to 500, more preferably about 3 to 100.

The monomer repeating units may be derived from an aliphatic hydroxy carboxylic acid or a related ester, lactone, dimeric ester, carbonate, anhydride, dioxanone, amide, or related monomer, preferably an aliphatic α-hydroxy carboxylic acid or related ester. Examples of such units include lactic acid, lactide, glycolic acid, glycolide, or a related aliphatic hydroxyl carboxylic acid, ester (lactone), dimeric acid or related compound such as, for example, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures thereof. The use of α-hydroxyacids and their corresponding cylic dimeric esters, especially lactide, glycolide, and caprolactone in the present invention, is preferred. It is noted that in using certain of the described monomers according to the present invention, the monomeric units which are produced are not specifically ester groups, but may include such groups as carbonate groups (polycarbonates), amino acids (which produce polyamides) and related groups which are derived from the above-described monomers or which contain a nucleophilic group and an electrophilic group and can be polymerized. It will be understood that the term polyester shall encompass polymers which are derived from all of the above monomers, with those which actually produce ester units being preferred.

The terms "poly(hydroxy carboxylic acid)" or "poly(α-hydroxy carboxylic acid)" are terms used to describe certain polyester A blocks of the {[A$_n$(BCB)A$_n$]E}$_m$ multi-block copolymers used in various embodiments of the present invention where A is a polymeric polyester unit derived from an aliphatic hydroxy carboxylic acid or a related ester or dimeric ester and is preferably derived from an aliphatic α-hydroxy carboxylic acid or related ester, including a cyclic dimeric ester, such as, for example, lactic acid, lactide, glycolic acid, glycolide, or a related aliphatic hydroxycarboxylic acid or ester (lactone) such as, for example, ε-caprolactone, δ-glutarolactone, δ-valerolactone, γ-butyrolactone and mixtures thereof, among numerous others as set forth herein. The use of α-hydroxyacids and their corresponding cylic dimeric esters, especially lactide and glycolide, is preferred.

Other suitable end-modified components may include, but are not limited to, ionizable polymers. The ionizable polymers used in the present invention may include linear, branched and/or crosslinked polymers, such as carboxyvinyl polymers of monomers such as acrylic acid, methacrylic acid, ethacrylic acid, phenyl acrylic acid, pentenoic acid and the like. Poly(acrylic acid) and its salts is a preferred carboxyvinyl polymer. One or more poly(carboxyvinyl) polymers may be used in a polyoxyalkylene composition. Copolymers, such as by way of example only, copolymers of acrylic acid and methacrylic acid, are also contemplated.

The reversely thermo-reversible hydrogel compositions made by either forming the complexes in water or by hydrating a dehydrated hydrogel or hydrating the complexes made by a hot melt processing method may include from approximately 5% to 20%, preferably from 8% to 18%, more preferably from 10% to 15% by weight of a water soluble block copolymer comprising at least two blocks of polyethylene oxide and at least one block of polypropylene oxide.

Associative Gelling Adjuvant

The term "associative gelling adjuvant" refers to an agent that modifies the gelling effect of other gelling agents while having few if any direct effects when added to a composition by itself. By nature, associative gelling adjuvants have very limited water solubility, and typically have a water solubility of less than 0.5 g/100 ml, preferably less than 0.3 g/100 ml, more preferably less than 0.1 g/100 ml at 20° C., and are not capable of viscosifying or gelling water when they are present in water by themselves.

With the currently commercially available Poloxamer polymers, the ability to obtain a sol-gel transition temperature lower than room temperature is limited at relatively low polymer concentrations. It is also desirable for gel compositions having low solid content to be able to carry and stabilize an effective amount of active ingredients for a controlled and sustained release of the active ingredients.

For example, about 20% w/w Pluronic® F 127 in water is needed to have a sol-gel transition temperature at about 25° C. To extend the sol-gel transition temperature far below 25° C., a higher concentration of block copolymer may be used. As high as 35% w/w Pluronic® F 127 may be needed to have a sol-gel transition temperature at about 8° C. In contrast, only about 18.5% Pluronic® F 127 in combination with about 8% laureth-4 may be needed to have the same sol-gel transition temperature. Due to the reduced polymer concentration, solution viscosity is much lower, and the resulting hydrogel is less tacky and exhibits much less residue, better shear sensitive property, and cosmetic effects.

In accordance with aspects of the present invention, it has been discovered that the gelling efficiency of water soluble block copolymers, comprising at least two blocks of polyethylene oxide and at least one block of polypropylene oxide, has been largely improved by addition of a small amount of at least one water insoluble associative gelling adjuvant. It has been discovered that although the relative amount of polymers used to form a reversely thermo-reversible gel at a desired temperature has been largely reduced, the resulting hydrogel compositions have improved capability of solubilizing and/or stabilizing an effective amount of pharmaceutical medicaments and cosmetic active ingredients that are sparingly soluble or insoluble in water.

It has been also discovered that the sol-gel transition temperatures of reversely thermo-reversible hydrogel compositions, comprising block copolymers having at least two blocks of polyethylene oxide and at least one block of polypropylene oxide, according to various embodiments of the present invention, may be regulated over a relatively wide temperature ranges under use conditions by incorporating an effective amount of at least one water insoluble associative gelling adjuvant. The ability to adjust the sol-gel transition temperature of the hydrogel compositions over a wide temperature range of use conditions with relatively low polymer concentration overcomes the limitations of state of the art hydrogel compositions and is advantageous because manufacturers have more flexibility in the selection of either a liquid state or gel form depending on the desired performance or handling properties of the composition. In particular, the present invention provides pharmaceutical, cosmetic and personal care compositions, having the properties set forth above, for the delivery of an effective amount of active ingredients with controlled or sustained release.

As mentioned above, it has been found that the advantageous properties of the hydrogel compositions may be maintained upon either re-hydrating compositions comprising the water-soluble supramolecular complexes following dehydration or by hydrating the complexes formed by a hot melt processing method. This is advantageous for the same reasons noted above, as the water-soluble supramolecular complexes according to the present invention may be manufactured and shipped less expensively due to the elimination of water weight. The water-soluble supramolecular complexes may then be mixed with water by the end user to achieve a gel or solution having the desired concentration.

In accordance with aspects of the present invention, it has been discovered that the formation of supramolecular complexes, comprising a block copolymer having at least two blocks of polyethylene oxide and at least one block of polypropylene oxide and at least one associative gelling adjuvant, have enhanced capability of solubilizing and/or stabilizing an effective amount of pharmaceutical medicaments and cosmetic active ingredients that are sparingly soluble or insoluble in water.

Examples of the associative gelling adjuvant, include, but are not limited to, oxyalkylated fatty alcohol, esters of oxyalkylated fatty alcohol, oxyalkylated alkyl alcohol, esters of oxyalkylated alkyl alcohol; oxyalkylated alkylaryl alcohol, aliphatic hydroxy carboxylic acid, ester of aliphatic hydroxy carboxylic acids, aromatic hydroxy carbolic acid esters of aromatic hydroxy carbolic acid, poly(hydroxy carboxylic acid), oxyalkylated sorbitan esters, oxyalkylated triglycerides, oxyalkylated glyceryl esters, esters of oxyalkylated sorbitol, polyol esters, sorbitan ester and the like.

Suitable associative gelling adjuvants for use herein include, but are not limited to, laureth-2, laureth-3, laureth-4, laureth-5, laureth-6, and the like; Oleth-2, Oleth-5, Oleth-10, and the like; $C_{12-13}$ pareth-2, $C_{12-13}$ pareth-3, $C_{12-13}$ pareth-4, $C_{12-13}$ pareth-5, $C_{12-13}$ pareth-6, and the like; di-PPG-2 myreth-9 adipate, di-PPG-2 myreth-10 adipate, di-PPG-2 myreth-11 adipate, and the like; salicylic acid and its derivatives; and the like.

An aspect of the present invention is that the sol-gel transition temperature of the hydrogel compositions containing the water-soluble supramolecular complexes may be regulated in the temperature range of from about 4-45° C., preferably from about 8-40° C., while having a sol-gel transition temperature greater than 45° C., by adjusting the ratio of the water soluble block copolymer to the associative gelling adjuvant at relatively low polymer concentrations. As noted above, the ability to adjust the sol-gel transition temperature of the hydrogel compositions overcomes the limitations of the state of the art and is very useful because it allows for a broad range of use temperatures of either a fluid or a gel state depending on the desired performance or handling properties.

When hydrated to form a reversely thermo-reversible hydrogel or solution composition, the water-soluble supramolecular complexes made according to various embodiments of the present invention may include from approximately 0.1% to 12%, preferably from 0.5% to 10%, more preferably from 1% to 8% by weight of at least one associative gelling adjuvant, said associative gelling adjuvant having a water solubility of less than 0.5 g/100 ml, preferably less that 0.3 g/100 ml, more preferably less than 0.1 g/100 ml, and being capable of forming water soluble inter-molecular complexes with said water soluble block copolymers.

In an exemplary embodiment, a hydrogel composition may be in the form of a gel or a liquid. Most preferably, the hydrogel composition exists as a gel or a liquid that is capable of gelling upon contact with dermal or mucosal tissue.

For some applications, the practical advantage of such reversely thermo-reversible hydrogel compositions is that the formulation can be administered as a flowing liquid at ambient temperatures. Upon contact with body tissues it gels, thus changing its flow properties, and more importantly, is not easily removed from the site of application.

For some other applications, the practical advantage of such reversely thermo-reversible hydrogel compositions is that the formulation can be administered as a gel at ambient temperature. The low solid content of hydrogel compositions containing water-soluble supramolecular complexes made according to various embodiments of the present invention results in a shear-sensitive characteristic and can be easily applied with dermal or mucosal tissue, and remains on the site for a prolonged period of time for the controlled or sustained release of active ingredients.

The water-soluble supramolecular complexes made according to embodiments of the present invention not only facilitates the administration of the formulation in some desired applications, but also helps to solubilize and/or stabilize sparely soluble or insoluble active ingredients. Due to its anhydrous form and the improved capability of solubilizing and/or stabilizing water insoluble or sparely soluble active ingredients, it has been discovered that a wide variety of useful pharmaceuticals medicaments and cosmetic active ingredients that are not ordinarily soluble in water can in fact be dissolved and/or stabilized in the supramolecular complexes of the present invention. For example, the use of salicylic acid or its derivatives for treating dandruff, acne, skin wrinkling, skin pigmentation, warts, freckles, or skin-related problems is well known in the preparation of dermatologic and cosmetic formulations. Salicylic acid or its derivatives are usually in crystalline form and are not sufficiently soluble in water or oils traditionally used in dermatological and cosmetic preparations. Typical problems which occur when using salicylic acid or its derivatives in making dermatologic and cosmetic products are that the salicylic acid or its derivatives tend to crystallize out within various compositions, which significantly reduces the bioavailability of salicylic acid or its derivatives for treating or preventing the aforementioned skin problems. The solution or hydrogel compositions containing water-soluble supramolecular complexes made according to the present invention may not only help to solubilize sparely soluble salicylic acid and its derivatives, but also prevent salicylic acid or its derivatives from crystallizing out within the compositions, which may significantly increase the bioavailability of salicylic acid or its derivatives for treating or preventing the aforementioned skin problems.

The hydrogel compositions containing water-soluble supramolecular complexes made according to the present invention exhibit many advantages. Due to the improved gelling efficiency across a broad temperature range of physiologically appropriate use conditions at relatively low polymer concentrations, they form clear and transparent gels and possess the appropriate thickness, emolliency, and cosmetic effect with a minimum of solids content. The hydrogel compositions containing water-soluble supramolecular complexes of the present invention remain clear and transparent before and after the transition to a gel state. In addition, very little residue is formed upon dehydration after application, which may be important in some applications. Furthermore, the hydrogel compositions have improved capability of solubilizing and/or stabilizing for otherwise insoluble additives. It has been discovered that a wide variety of useful pharmaceuticals medicaments and cosmetic active ingredients that are not ordinarily soluble in water can in fact be dissolved and/or stabilized and/or dispersed and/or suspended in the hydrogel compositions of the present invention. In many circumstances, an alcohol free hydrogel composition may be formulated due to the enhanced solubilizing and/or stabilizing ability of hydrogel compositions containing water-soluble supramolecular complexes of the present invention. In some instances, the addition of other auxiliary solubilizers/compatibilizers may be helpful, if the desired sol-gel transition temperature is maintained.

According to another embodiment of the present invention a wet method is provided for preparing a solid composition containing the water-soluble supramolecular complexes, comprising the steps of:
  (a) Dissolving a water soluble block copolymer in water at a temperature below 20° C.,
  (b) Then mixing the dissolved copolymer with at least one associative gelling adjuvant at a suitable temperature to form a transparent hydrogel or solution, and
  (c) drying the transparent hydrogel or solution until at least 45%, more preferably at least 75%, and most preferably at least 95% of the water is removed from the transparent hydrogel or solution.

The method employed to dehydrate the transparent hydrogel may be any method that will not negatively affect the properties of the water-soluble supramolecular complexes. Examples of such drying techniques include heat drying, vacuum drying, spray drying, and freeze drying methods or combination thereof.

According to yet another embodiment of the present invention, a hot melt processing method for preparing a solid composition containing the water-soluble supramolecular complexes is provided. The hot melt processing method does not require the presence of water to form the complexes and comprises:
  (a) heating the water soluble block copolymer to a temperature of 55 to 120° C.,
  (b) mixing the heated copolymer with at least one associative gelling adjuvant at a temperature of 55 to 120° C. to form a mixture, and
  (c) cooling the mixture.

The partially or wholly anhydrous solid material obtained through either the wet method or the hot melt process may then be dissolved in water to form a clear and transparent solution or gel depending on the concentration without any precipitation of insoluble material.

Pharmaceutical Medicament

As those skilled in the art will appreciate, the water-soluble supramolecular complexes of the present invention may be utilized as drug delivery vehicles for administering a variety of pharmaceutical drugs, and diagnostic compounds. The solid compositions containing the water-soluble supramolecular complexes may be combined with an effective amount of a pharmaceutical drug or diagnostic compound to provide various dosage forms, such as a solid dosage form, a gel form, or a solution form.

Suitable pharmaceutical drugs and diagnostic compounds for incorporating into the water-soluble supramolecular complexes drug delivery compositions according to the present invention may be water soluble, sparely soluble in water, and insoluble pharmaceutical compounds. Exemplary pharmaceutical drugs, therapeutic agents or diagnostic agents which may be administered by the water-soluble supramolecular complexes according to of the present invention include, but are not limited to:

(1) Antibacterial substances such as beta-lactam antibiotics, such as cefoxitin, n-formamidoyl-thienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin, sulfonamides; aminoglycoside antibiotics such as gentamycin, kanamycin, amikacin, sisomicin and tobramycin; nalidixic acid and analogs such as norfloxacin and the antimicrobial combination of flucalanine/pentizidone; nitrofurazones, and the like;

(2) Antihistaminics and decongestants such as pyrilamine, chlorpheniramine, tetrahydrazoline, antazonline, and the like;

(3) Anti-inflammatorics such as cortisone, hydrocortisone, hydrocortisone acetate, betamethasone, dexamethasone, dexamethasone sodium phosphate, prednisone, methylpredinisolone, medrysone, fluorometholone, fluocortolone, prednisolone, prednisolone sodium phosphate, triamcinolone, indomethacin, sulindac, its salts and its corresponding sulfide, and the like;

(4) Miotics and anticholinergics such as echothiophate, pilocarpine, physostigmine salicylate, diisopropylfluorophosphate, epinephrine, dipivolyl epinephraine, neostigmine, echothiophate iodide, demecarium bromide, carbachol, methacholine, bethanechol, and the like;

(5) Mydriatics such as atropine, homatropine, scopolamine, hydroxyamphetamine, ephedrine, cocaine, tropicamide, phenylephrine, cyclopentolate, oxyphenonium, eucatropine, and the like; and other drugs used in the treatment of eye conditions or diseases such as (6) Antiglaucoma drugs, for example, betaxalol, pilocarpine, timolol, especially as the maleate salt and R-timolol and a combination of timolol or R-timolol with pilocarpine. Also included are epinephrine and epinephrine complex or prodrugs such as the bitartrate, borate, hydrochloride and dipivefrin derivatives and hyperosmotic agents such as glycerol, mannitol and urea;

(7) Antiparasitic compounds and/or anti-protozoal compounds such as ivermectin; pyrimethamine, trisulfapyrimidine, clindamycin and corticosteroid preparations;

(8) Antiviral effective compounds such as acyclovir, 5-iodo-2'-deoxyuridine (IDU), adenosine arabinoside (Ara-A), trifluorothymidine, and interferon and interferon inducing agents such as Poly I:C;

(9) Carbonic anhydrase inhibitors such as acetazolamide, dichlorphenamide, 2-(p-hydroxyphenyl) thio-5-thiophenesulfonamide, 6-hydroxy-2-benzothiazolesulfonamide and 6-pivaloyloxy-2-benzothiazolesulfonamide;

(10) Anti-fungal agents such as clotrimzole, fluconazole, flucytosine, itraconazole, ketoconazole, miconazole, ciclopirox, econazole, nystatin, oxiconazole, terbinafine Hydrochloride, tioconazole, butoconzle, terconazole, miconazole nitrate, metronidazole, isoconazole nitrate, and tolnaftate.
(11) Anesthetic agents such as etidocaine cocaine, henoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;
(12) Ophthalmic diagnostic agents such as: (a) Those used to examine the retina and chloride-sodium fluorescein; (b) Those used to examine the conjunctive, cornea and lacrimal apparatus such as fluorescein and rose bengal; and (c) Those used to examine abnormal pupillary responses such as methacholine, cocaine, adrenaline, atropine, hydroxyamphetamine and pilocarpine;
(13) Ophthalmic agents used as adjuncts in surgery such as alphachymotrypsin and hyaluronidase;
(14) Chelating agents such as ethylenediamine tetraacetate (EDTA) and deferoxamine;
(15) Immunosuppressive agents and anti-metabolites such as methotrexate, cyclophosphamide, 6-mercaptopurine, and azathioprine;
(16) Peptides and proteins such as atrial natriuretic factor, calcitonin-gene related factor, lutinizing hormone, releasing hormone, neuroterisin, vasoactive intestinal peptide, vasopressin, cyclosporine, Botulinum toxin, interferon, substance P enkephalins, epidermal growth factor, eyederived growth factor, fibronectin, insulin-like growth factor and mesodermal growth factor;
(17) Acne treatment agents, such as salicylic acid and its derivatives, sulfur, lactic acid, glycolic, pyruvic acid, azelaic acid, benzoyl peroxide, urea, resorcinol and N-acetylcysteine, and retinoids, such as retinoic acid, and its derivatives, and the like;
(18) Lubricating agents such as sodium hyaluronate or polyvinyl alcohol; and
(19) Combinations of the above such as antibiotic/anti-inflammatory as in neomycin sulfate-dexamethasone sodium phosphate, concomittant anti-glaucoma therapy such as timolol maleate-aceclidine.

As those skilled in the art will appreciate, the foregoing list of pharmaceutical compounds is exemplary only. Because the drug delivery compositions containing the water-soluble supramolecular complexes according to the present invention are uniquely suited for utilization in a wide variety of physiological applications such as the ocular, oral, nasal, rectal or subcutaneous administration of pharmaceutical compounds, a wide variety of pharmaceutical medicaments may be incorporated therein. Accordingly, the foregoing list of pharmaceutical medicaments is not intended to limit the scope of the present invention and is exemplary only.

The water-soluble supramolecular complexes according to the present invention are most suitable for the pharmaceutical drugs which exhibit poor bioavailability, such as levobunolol, pilocarpine, dipivefrin, and others.

Preferably, the water-soluble supramolecular complexes according to the present invention may include from approximately 0.01% to 70%, preferably from 0.05% to 50%, and more preferably from 0.1% to 30% by weight of pharmaceutical drugs and diagnostic compounds. To prepare the water-soluble supramolecular complexes containing pharmaceutical drugs and diagnostic compounds, an effective amount of pharmaceutical drugs and diagnostic compounds of choice may be incorporated either by wet process and then subsequently dehydrated or a hot melt process.

Preferably, when utilized as a solid dosage or hydrogel drug delivery vehicle for topical application, drop instillation, oral administration or injection, the compositions containing the water-soluble intermolecular complexes according to the present invention may be modified to include from approximately 0.01% to 70%, preferably 0.05% to 50%, and more preferably from 0.1% to 30% by weight of the pharmaceutical drug or diagnostic agent. To prepare a drug delivery vehicle in accordance with the present invention, an appropriately effective amount of the pharmaceutical compound of choice is simply incorporated into the composition at the composition formulation temperatures and pHs. Preferably, the compound of choice is soluble in the solution or is homogeneously dispersed. Soluble pharmaceutical compounds may readily dissolve in the composition, whereas insoluble compounds may preferably be pulverized for even dispersion throughout the compositions. Along these lines, it is also contemplated as being within the scope of the present invention to incorporate insoluble or erodible micro-particulate drug delivery systems into the compositions, such as those known in the art. In this manner, controlled release drug delivery systems can be incorporated into the compositions containing the water-soluble intermolecular complexes of the present invention and retained in position when administered by drop or injection.

In some embodiments, the compositions containing the water-soluble intermolecular complexes according to the present invention may comprise traditional Chinese herb medicines or Chinese herb extracts. The traditional Chinese herb medicines may be pulverized, uniformly dispersed and/or suspended in the hydrogel composition. The hydrogel compositions may serve not only as an effective dispersion and/or suspension medium as drug delivery vehicles, but also are capable of extracting the herb actives from the various traditional Chinese herb medications.

Pharmaceutically acceptable excipients that can be included in the pharmaceutical hydrogel compositions containing the water-soluble supramolecular complexes according to the present invention include, but are not limited to, for example, physiologically tolerable surfactants, solvents, humectants, emollients, penetration enhancers, colorants, fragrances, and the like, which are well known in the art. The hydrogel compositions preferably have a pH value in the range of about 1 to about 12. Other preferred embodiments may have a pH value in the range of about 3.5 to about 10.

Particular pharmaceutical applications and formulations may include the following.

Esophageal, oral cavity and buccal applications: The compositions containing the water-soluble supramolecular complexes according to the present invention provide a suitable vehicle for delivering drugs within the esophageal lining; Ophthalmic applications: Hydrogel formulations may be applied as drops which gel upon contact with eye or as a shear sensitive gel. Since gelling may be accomplished with low concentrations of the polymer, blurring may be minimized upon drop instillation; Nasal applications: Hydrogel formulation compositions can be readily sprayed in a liquid state at low temperatures, and the subsequent gelation occurs only after administration of the formulation and only at the site of application; Vaginal/rectal applications: compositions may increase the residence time of formulations, and prevent the leak-back that is a typical undesired effect of current formulations.

Veterinary applications: The compositions containing the water-soluble supramolecular complexes according to the present invention also may be useful in the treatment of not only human conditions, but in providing treatments for animal care. For veterinary products, hydrogel compositions indicated for the preparation of topical dermal products, such as antibacterials, antifungals, antipruritics, and antiseborrhea, antiodor, and antiseptic/wound healing preparations. Otic products would include ear cleansers with or without actives, such as, antifungals. Ophthalmic products would include eye moisturizers or antimicrobial preparations.

Tablet or gel capsules: The water-soluble supramolecular complexes containing active pharmaceutical ingredients according to the present invention may be introduced in powder form into a tablet along with other ingredients. Solid compositions containing the water-soluble supramolecular complexes along with active ingredients and other ingredients may also be formed or encapsulated.

Injectibles: A depot formulation containing the water-soluble supramolecular complexes according to the present invention may be prepared and administered at low viscosity to a subdermal or intramuscular site, which will slowly release the active ingredient for a sustained or extended period; alternatively, a hydrogel composition containing the water-soluble supramolecular complexes according to the present invention and the active ingredients may be prepared in a gel form to suspend microspheres or particles in a formulation. The formulation may then take advantage of the shear thinning properties of the hydrogel composition. Thus, during injection, the formulation is subjected to shear stresses, which reduce viscosity and allow an ordinarily viscous formulation to be introduced into the patient by injection. Cessation of the strain results in reestablishing the high viscosity of the gel form of the formulation, so that the active agent may be slowly released therefrom.

Preparation of pharmaceutical compositions may be accomplished with reference to any of the pharmaceutical formulation guidebooks and industry journals, which are available in the pharmaceutical industry. These references supply standard formulations, which may be modified by the addition or substitution of the compositions containing the water-soluble supramolecular complexes according to the present invention into the formulation. Suitable guidebooks include Pharmaceutics and Toiletries Magazine, Vol. 111 (March, 1996); Formulary: Ideas for Personal Care; Croda, Inc, Parsippany, N.J. (1993); and Pharmaceuticon: Pharmaceutic Formulary, BASF, which are hereby incorporated in their entireties by reference.

The pharmaceutical composition may be in any form. Suitable forms will be dependent, in part, of the intended mode and location of application. Ophthalmic and otic formulations are preferably administered in droplet or liquid form; nasal formulations are preferable administered in droplet or spray form, or may be administered as a powder (as a snuff); vaginal and rectal formulations are preferably administered in the form of gel, thick liquid, or a suppository; oral formulations are preferred in tablet, capsule, or liquid forms; veterinary formulations may be administered as a gel, liquid, cream, lotion, or spray; esophageal and buccal/oral cavity applications are preferably administered from solution, as a solid dosage, or as a powder; film forming applications or dermal applications may be administered as a liquid, cream, lotion, soft gel, hard gel sticks, roll-on formulations, or pad-applied formulations.

Exemplary drugs or therapeutics delivery systems which may be administered using a composition containing the water-soluble supramolecular complexes according to the present invention include, but are in no way limited to, mucosal therapies, such as esophageal, otic, rectal, buccal, oral, vaginal, and urological applications; topical therapies, such as wound care, skin care and teat dips; and intravenous/subcutaneous therapies, such as intramuscular, intrabone (e.g., joints), spinal and subcutaneous therapies, tissue supplementation, adhesion prevention and parenteral drug delivery. In addition, further applications include transdermal delivery and the formation of depots of drug following injection. The pharmaceutical medicaments are most suitably absorbable through skin or mucosal membranes.

The wet method and hot processing method described above may also be used to prepare pharmaceutical compositions in the form of a solid, liquid, or gel by incorporating the pharmaceutical medicament or diagnostic compound either prior to, contemporaneously with, and/or following the addition of the gelling adjuvant. Upon obtaining a formulation by the wet method, the composition may be optionally dried to be used in solid dosage form or subsequently rehydrated to be used in liquid or gel form. The hot processing method will be used either in solid dosage form or simply require the addition of water to form a gel or liquid form.

Cosmetic Active Ingredients

As those skilled in the art will appreciate, the solid form, hydrogel, or solution compositions containing the water-soluble supramolecular complexes according to the present invention may further comprise about 0.01-70%, preferably about 0.1-50%, by weight of the total composition of cosmetic active ingredients. The cosmetic may be skincare products such as facial hydrogels, hands and foot care hydrogels; acne treatment hydrogels, shaving hydrogels, cleansing hydrogels; powders, antiperspirants; hair remover hydrogels, tooth whitening hydrogels, color makeup products such as makeup base, hydrogel foundation, eye shadow, eyeliner, blush; sun screen hydrogels; insect repellants, and the like.

Suitable cosmetic active ingredients for incorporating into the solid form, hydrogel, or solution compositions include essential oils, moisture retention agents, skin-beautifying agents, sun screen, antiperspirants, vitamins, amino acids, anti-acne agents, antiseptics or antibacterial agents, zinc salts, tooth whitening agents, depilatory agents, fragrance oils, insect repellants, antioxidants, chelating agents, refrigerants, anti-inflammatory agents, salts, colorants, and particulate fillers. Exemplary cosmetic active ingredients which can be incorporated into the hydrogel compositions include, but are not limited to:

(1) Essential oils including, but not limited to, almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, tea tree oil and tangerine oil. Alternatively, active agents found in essential oils such as, but not limited to, 1-citronellol, α-amylcinnamaldehyde, lyral, geraniol, farnesol, hydroxycitronellal, isoeugenol, eugenol, eucalyptus oil and eucalyptol, lemon oil, linalool, and citral may be used. Apart from their effects as fragrances or flavorants, such compounds also may be useful in the compositions as antimicrobial agents. The concentrations of essential oils or isolated components may be between about 0.3 and 1 wt. % or between about 0.1 and 0.5 wt. % or between 0.5 and 2 wt. %.

(2) Moisture retention agents include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside, and the like;

(3) Skin-beautifying agents include whitening agents such as placenta extract, arbutin, glutathione and Yukinoshita extract, kojic acid, placenta extract, sulfur, ellagic acid, linoleic acid, tranexamic acid; cell activators, such as royal jelly, photosensitizers, cholesterol derivatives, calf blood extract, α-hydroxy acid and β-hydroxy acid; rough and dry skin improvers; blood circulation improvers, such as nonylic acid vanillyl amide, benzyl nicotinate, β-butoxyethyl nicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and γ-oryzanol; skin astringents, such as zinc oxide and tannic acid; and anti-seborrheic agents, such as sulfur and thianthol; and skin colorants such as α-hydroxyacetone, and the like;

(4) Sun screen include UV absorbents of benzoate type, such as p-aminobenzoic acid, ethyl dihydroxypropyl p-aminobenzoate, glyceryl p-aminobenzoate, and octyl p-dimethylaminobenzoate; anthranilic acid type UV absorbents such as methyl anthranilate; UV absorbents of salicylic acid type, such as methyl salicylate, octyl salicylate, and triethanol amine salt or salicylic acid; cinnamic acid type UV absorbents, such as octyl p-methoxycinnamate, diethanol amine salt of p-methoxyhydroxycinnamic acid, and dimethocynnamic acid/isooctanoic acid gryceride; benzophenone type UV absorbents, such as 2,4-dihydroxybenzophenon, 2,2',4,4'-tetrahydroxybenzophenon, 2-hydroxy-4-methyoxybenzophenon, 2-hydroxy-4-methoxypenzophenon-5-sulfonic acid, 2,2'-dihydroxy-4-methoxypenzophenon, and 2-hydroxy-4-N-octoxybenzophenon; UV absorbents of urocanic acid type, such as ethyl urocanate; UV absorbents of dibenzoylmethane type, such as 4-tert-butyl-4'-methoxydibenzoylmethane, 4-isopropyl dibenzoylmethane; 3-(4-methylbenzylidene) camphor, octyltriazone, e-ethylhexyl-2-cyano-3,3-diphenylacrylate, 2-phenylbenzoimidasole-5-sulfate, 4-(3,4-dimethoxypnehylmethylene)-2,5-dioxo-1-imidazolidine, and 2-ethylhexylpropionate. The UV absorber may be encapsulated in a polymer powder. The aforesaid powders which absorb or scatter UV ray may be used, for example, titanium oxide fine powder, fine powder of titanium oxide containing iron, zinc oxide fine powder, cerium oxide fine powder and a mixture thereof, and the like;

(5) Antiperspirants include aluminum chlorohydrate, aluminum chloride, aluminum sesquichlorohydrate, zirconyl hydroxy chloride, aluminum zirconium hydroxychloride and aluminum zirconium glycine, and the like;

(6) Vitamins include vitamin A such as vitamin A oil, retinol, retinyl acetate and retinyl palmitate; vitamin B2 such as riboflavin, riboflavin butyrate and flavin adenine nucleotide, vitamin B6 such as pyridoxine hydrochloride, pyridoxine dioctanoate and pyridoxine tripalmitate, vitamin B12 and its derivatives, and vitamin B15 and its derivatives; vitamin C, such as L-ascorbic acid, L-ascorbate dipalmitate, sodium (L-ascorbic acid)-2-sulfate and dipotassium L-ascorbic acid diphosphate; vitamin D, such as ergocalciferol and cholecarciferol; vitamin E, such as α-tocopherol, β-tocopherol, γ-tocopherol, dl-α-tocopheryl acetate, dl-α-tocopheryl nicotinate and dl-α-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; biotin, and the like;

(7) Amino acids include glycine, valine, leucine, isoleucine, serine, threonine, phenylaranine, alginine, lysine, aspartic acid, glutamic acid, cystine, cysteine, methionine, and tryptophan; examples or the nucleic acids include deoxyribonucleic acid; and examples of the hormones include estradiol and ethenyl estradiol, and the like;

(8) Anti-acne agents, such as salicylic acid and its derivatives, sulfur, lactic acid, glycolic, pyruvic acid, azelaic acid, benzoyl peroxide, urea, tea tree oil, resorcinol and N-acetylcysteine, and retinoids, such as retinoic acid, and its derivatives, and the like;

(9) Antiseptics or antibacterial agents include alkyl paraoxybenzoates, benzoic acid, sodium benzoate, sorbic acid, potassium sorbate, and phenoxyethanol may be used. For the antibacterial agents, benzoic acid, benzyl peroxide, salicylic acid and its derivatives, carbolic acid, sorbic acid, paraoxybenzoic acid alkyl esters, parachloromethacresol, hexachlorophene, benzalkonium chloride, chlorohexydine chloride, trichlorocarbanilide, triclosan, photosensitizer, phenoxyethanol, and the like;

(10) Zinc salts as anti-viral and anti-bacterial agents, and also for reducing or preventing skin irritation. Examples of Zinc salts include zinc acetate, zinc lactate, zinc propionate, zinc gluconate and zinc oxide as those described in U.S. Pat. No. 5,208,031, the disclosure of which is hereby incorporated by reference. The zinc salts may be included at a concentration of between 0.5-25%.

(11) Tooth whitening agents include, but are not limited to, hydrogen peroxide, carbimide peroxide, calcium peroxide, percarbonate, sodium percarbonate, perborates, persulfates, and mixtures thereof. Oxalic acid, malonic acid, tartaric acid and salts thereof. Suitable dicarboxylic acid salts include, but are not limited to, sodium, potassium, zinc, iron, calcium, magnesium, and copper salts of, e.g., oxalic acid, malonic acid and tartaric acid.

(12) Depilatory agents include, but are not limited to, thiol-based depilatory agents such as one or more thiol acids, (e.g. thioglycolic, thiolactic acid, and β-mercaptopropionic acid), or the alkali and/or the alkaline-earth metal salts of these acids. In addition, other active thiol agents can be used. These include β-mercaptoethanol, thioglycerols, 1,3-dithio-2-propanol, 1,4-dithio-2-butanol, 1,4-dimercapto-2,3-butanediol, 1,3-diexthio-2-methoxypropane, 1,3-dimercapto-2-aminopropane, 1,4-dimercapto-2,3-diaminobutane, aminoethanethiol, and related effective thiol actives, and the like.

(13) Fragrance oils include fragrance oils from synthetic, natural, and mixtures thereof. The perfume hydrogel compositions may be applied either as a rub in hydrogel or a spray for a sustained release of fragrance scents with or without alcohol.

(14) Insect repellants include ethyl butylacetylaminopropionate, N, N-diethyl toluamide (DEET), N, N-diethyl benzamide, dimethyl phytate, ethyl bexanediol, indalone, bicycloheptene dicarboxide, tetrahydro furaldehyde, and the like.

(15) Antioxidants include tocopherol, butylhydroxyanisole, dibutylhydroxytoluene and phytic acid;

(16) Examples of the chelating agents include alanine, sodium ethylenediaminetetraacetate, sodium polyphosphate, sodium metaphosphate and phosphoric acid;
(17) Examples of the refrigerants include L-menthol and camphor;
(18) Examples of the anti-inflammatory agents include allantoin, glycyrrhizin and salts thereof, glycyrrhetinic acid and stearyl glycyrrhetinate, tranexamic acid, azulene, and the like;
(19) Salts such as inorganic salts, salts of organic acid, amine salts and salts of amino acid. Examples of the inorganic salts include sodium, potassium, magnesium, calcium, aluminum, zirconium, and zinc salt of hydrochloric acid, sulfuric acid, carbonate acid, and nitric acid. Examples of organic acid salts include salts of acetic acid, dehydroacetic acid, citric acid, maleic acid, succinic acid, ascorbic acid, and stearic acid. An example of amine salt is salt of triethanolamine and that of amino acid salt is salt of glutamic acid. Other examples are salts of hyaluronic acid, chondroitin sulfate, aluminum zirconium glycine complex and salts made by acid-base reaction which are allowed to incorporate in cosmetics.
(20) Colorants include various dyes, organic and inorganic pigments. Examples of dyes include azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors; and carbon black. Inorganic pigments include iron oxides, ultramarines, chromium, chromium hydroxide colors, and mixtures thereof. Suitable inorganic pigments include iron oxides.
Mention may also be made of colorants with an effect, such as particles comprising a natural or synthetic, organic or mineral substrate, for example glass, acrylic resins, polyester, polyurethane, polyethylene terephthalate, ceramics or aluminas, the said substrate being uncoated or coated with metallic substances, for instance aluminum, gold, silver, platinum, copper or bronze, or with metal oxides, for instance titanium dioxide, iron oxide or chromium oxide, and mixtures thereof. Interference pigments, especially liquid-crystal or multilayer interference pigments may also be used.
The water-soluble dyes are, for example, beetroot juice or methylene blue.
Other colorants may be encapsulated with water soluble materials or water insoluble materials. Products such as SUNSIL materials, encapsulated with silicone, are available from Sunjin Chemical Company. Additional dyestuffs coated with nylon or polymethyl methacrylate are also available from Sunjin Chemical Company.
(21) Particulate fillers may be colored or non-colored (non-colored meaning without color or white in color), preferably, the particulate fillers have particle size of 0.02 to 100, preferably 0.5 to 50 microns. Suitable particulate fillers include bismuth oxychloride, titanated mica, fumed silica, spherical silica, silicone powder, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silk powder, silica, talc, mica, titanium dioxide, zinc laurate, zinc myristate, zinc rosinate, alumina, attapulgite, calcium carbonate, calcium silicate, dextran, kaolin, nylon, silica silylate, sericite, soy flour, tin oxide, titanium hydroxide, trimagnesium phosphate, walnut shell powder, or mixtures thereof.
(22) The above mentioned pigments and particulate fillers may be surface treated with lecithin, amino acids, mineral oil, silicone oil or various other agents either alone or in combination, which coat the particulate surface. The coating used for the surface treatment may be either lipophilic or hydrophilic in character.

As those skilled in the art will appreciate, the foregoing listing of cosmetic active ingredients is exemplary only. The cosmetic compositions containing the water-soluble supramolecular complexes according to the present invention are uniquely suited for utilization in a wide variety of cosmetic and personal care products and applications for beauty and personal care.

In some embodiments, the compositions containing water-soluble supramolecular complexes may comprise pharmaceutical and/or physiologically acceptable humectants which are preferably present at a level of about 0.01% to 40%, more preferably about 0.1% to 30%, and most preferably about 0.5% to 25%. Preferred humectants include, but are not limited to, compounds selected from polyhydric alcohols, sorbitol, glycerol, urea, betaine, D-panthenol, DL-panthenol, calcium pantothenate, royal jelly, panthetine, pantotheine, panthenyl ethyl ether, pangamic acid, pyridoxin, pantoyl lactose Vitamin B complex, sodium pyrrolidone carboxylic acid, hexane-1,2,6, -triol, guanidine or its derivatives, and mixtures thereof.

Suitable polyhydric alcohols for use herein include, but are not limited to polyalkylene glycols and preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, pentylene glycol, hexylene glycol, butylene glycol (e.g., 1,3-butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. Preferred polyhydric alcohols may be selected from glycerine, butylene glycol, propylene glycol, pentylene glycol, hexylene glycol, dipropylene glycol, polyethylene glycol, hexane triol, ethoxylated glycerine and propoxylated glycerine and mixtures thereof.

Suitable humectants useful herein also include sodium 2-pyrrolidone-5-carboxylate (NaPCA), guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; betaine, panthenol and derivatives thereof; and mixtures thereof.

In some embodiments, the compositions containing the water-soluble supramolecular complexes according to the present invention may comprise pharmaceutical and/or physiologically acceptable emollients, which are preferably present at a level of about 0.01% to 20%, preferably about 0.1% to 15% and preferably about 0.5% to 10%. Examples of emollients are lanolin, castor oil, mineral oil, silicone derivatives and petroleum jelly. Other emollients include high oleic sunflower oil and its derivatives, macadamia nut oil and its derivatives, grape seed oil, hazelnut oil, olive oil, sesame oil, and other natural seed and nut oils, such as jojoba oil, and derivatives thereof. Finally, other emollients include corn oil, cottonseed oil, rose water ointment, apricot kernel oil, avocado oil, *theobroma* oil, almond oil, and myristyl alcohol. Additionally, a number of fatty acids derived from either plants or animal sources have been used as emollients. Fatty acids used in cosmetic formulations include stearic acid, oleic acid, myristic acid and palmitic acid. Other typical fatty acids include linoleic acid, behenic acid, and palmitoleic acid. Fatty alcohols are also used as emollients. Examples of fatty alcohols used as emollients are lauryl alcohol, cetyl alcohol, stearyl alcohol, jojoba alcohol and oleyl alcohol. Further, fatty esters are used as emollients. Examples of fatty esters include isopropyl palmitate, isopropyl myristate and glyceryl stearate. Another fatty ester emollient is ojoba oil. Further, non-biodegradable emollients, such as hydrocarbons or silicones (such as methyl silicones) are known and are used as emollients in cosmetic and personal care preparations.

In some embodiments, the compositions containing the water-soluble supramolecular complexes according to the present invention may further comprise surfactants which are preferably present at a level of about 0.01% to 15%, preferably about 0.1% to 10%. The surfactant may be an anionic surfactant, a cationic surfactant, an ampholytic surfactant, or a nonionic surfactant. Examples of nonionic surfactants include fatty acid esters of polyols, for-instance sorbitol or glyceryl mono-, di-, tri- or sesqui-oleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl) ethers. Examples of anionic surfactants include carboxylates (sodium 2-(2-hydroxyalkyloxy) acetate)), amino acid derivatives (N-acylglutamates, N-acylglycinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof. Examples of amphoteric and zwitterionic include betaines, N-alkylamidobetaines and derivatives thereof, glycine derivatives, sultaines, alkyl polyaminocarboxylates and alkylamphoacetates, and mixtures thereof.

In some embodiments, the compositions containing the water-soluble supramolecular complexes according to the present invention may further comprise rheology modifiers which are preferably present at a level of from about 0.01% to about 6%. Examples of rheology modifiers include, but not limited to, carbomers, acrylic copolymers, polyacrylamides, polysaccharides, natural gums, clays such as Laponite® from Southern Clay Products, Inc. (Gonzales, Tex.), and the like.

In some embodiments, the compositions containing the water-soluble supramolecular complexes according to the present invention may comprise one or more components that facilitate penetration through the upper stratum corneum barrier to the lower levels of the skin. Examples of skin penetration enhancers include, but are not limited to, propylene glycol, azone, ethoxydiglycol, dimethyl isosorbide, urea, ethanol, dimethyl sulfoxide, and the like.

In some embodiments, the compositions containing the water-soluble supramolecular complexes according to the present invention may comprise water-soluble film-forming polymers and may include, but are not limited to, amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic poly vinyl acetate type such as vinyl acetate/crotonic acid copolymer; acidic acrylic polymers such as (meth) acrylic acid/alkyl (meth) acrylate copolymer, (meth) acrylic acid/alkyl (meth)acrylate/alkyl acrylic amide copolymer, and amphoteric acrylic polymer such as N-methacryloylethyl-N,N-dimethylammonium alpha-N-methylcarboxybetaine/alkylmethacrylate copolymer, hydroxypropyl (meth)acrylate/butylaminoethyl methacrylate/octyl amide of acrylic acid copolymer. Suitable water-soluble polymers are also preferably chosen from: proteins, for instance proteins of plant origin, such as wheat proteins and soya proteins; proteins of animal origin, such as keratin, for example keratin hydrolysates and sulphonic keratins; anionic, cationic, amphoteric or nonionic chitin or chitosan polymers; cellulosic polymers, such as hydroxyethylcellulose, hydroxypropylcellulose, methylcellulose, ethylhydroxyethylcellulose and carboxymethylcellulose, and quaternized cellulose derivatives; polymers of natural origin, which are optionally modified, such as: gum arabic, guar gum, xanthan derivatives, karaya gum; alginates and carrageenans; glycosaminoglycans, hyaluronic acid and derivatives thereof; shellac, sandarac gum, dammar resins, elemi gums and copal resins; deoxyribonucleic acid; mucopolysaccharides such as hyaluronic acid and chondroitin sulphate, and mixtures thereof.

In some embodiments, the compositions of the present invention may comprise preservatives. Example of physiologically tolerable preservatives include, but are not limited to, bacteriostats, preservatives, inhibitors, and the like, such as methyl, ethyl, propyl, and butyl esters of parahydroxybenzoic acid (paraben); propyl gallate; sorbic acid and its sodium and potassium salts; propionic acid and its calcium and sodium salts; 6-acetoxy-2,4-dimethyl-m-dioxane; 2-bromo-2-nitropropane-1,3-diol; salicylanilides such as dibromosalicylanilide and tribromosalicylamilide; hexachlorophene; sodium benzoate; chelating agents such as ethylene diaminetetraacetic acid (EDTA), citric acid, and their alkali metal salts; phenolic compounds such as butyl hydroxyanisol, butyl hydroxytoluene, chloro- and bromo-cresols, and chloro- and bromo-oxylenols; quaternary ammonium compounds such as benzalkonium chloride; aromatic alcohols such as 2-phenylethyl alcohol and benzyl alcohol; chlorobutanol; quinoline derivatives such as iodochlorohydroxyquinoline; and the like.

In some embodiments, the compositions containing the water-soluble supramolecular complexes according to the present invention may comprise pH regulators such as lactic acid, citric acid, glycolic acid, succinic acid, tartaric acid, dl-malic acid, potassium carbonate, sodium hydrogen carbonate and ammonium hydrogen carbonate. Acids or bases may also be used to adjust the pH of these formulations as needed. Various pH regulators and means for adjusting pH may be used so long as the resulting preparation is pharmaceutically and cosmetically acceptable. The hydrogel compositions preferably have a pH value in the range of about 1 to about 12. Other preferred embodiments may have a pH value in the range of about 3.5 to about 10.

In some embodiments, the compositions may comprise hair coloring agents that may include, but are not limited to, oxidative dyes, photographic dyes, acid dyes, neutral dyes, reactive dyes, cationic dyes, VAT dyes, and mixtures thereof, as those described in U.S. Pub. NO.: 2004/0158941, the disclosure of which is hereby incorporated by reference. A preferred hair coloring agent herein is an oxidative hair coloring agent. The total combined level of oxidative hair coloring agents in the hydrogel compositions according to the present invention is about 0.001% to 5%, preferably about 0.01% to 4%, more preferably about 0.1% to 3%, most preferably about 0.1% to 1% by weight.

The hair coloring compositions containing the water-soluble supramolecular complexes according to the present invention may preferably also comprise at least one oxidizing agent, which may be an inorganic or organic oxidizing agent as those described in U.S. Patent Pub. No.: 2004/0158941, the disclosure of which is hereby incorporated by reference. The oxidizing agent may preferably be present at a level about 0.01% to 10%, preferably about 0.1% to 6%, more preferably about 1% to 4% by weight of the composition.

Various embodiments may also comprise additional additives, including but not limited to, silicone components such as silicone oils (such as dimethicone or cyclomethicone), water-soluble dimethicone coplyols, silicone elastomer, and emulsifier silicone elastomer, and the like. Examples of suitable silicone elastomers include those sold under the names KSG from Shin-Etsu, Trefil E-505C, Trefil E-506C, DC 9506 or DC 9701 from Dow-Corning, and those described in U.S. Pat. No. 5,266,321, the disclosure of which is incorporated by reference herein. Emulsifying elastomers may include those sold under the names of KSG-210, KSG-30, KSG-31, KSG-32, KSG-33, KSG-40, KSG-41, KSG-42, KSG-43, KSG-44 and KSG-710 from Shin-Etsu, or coated elastomers, such as products sold under the denomination KSP (for example, KSP-100, KSP-200, KSP-300) sold by Shin Etsu and/or those described in U.S. Pat. No. 5,538,793, the disclosure of which is hereby incorporated by reference. A mixture of these commercial products may also be used. If present, the elastomeric compounds are preferably present in an amount of 0.01% to 15%, preferably from 0.1% to 10%.

In still other embodiments of the present invention, the compositions containing the water-soluble supramolecular complexes may be formulated and applied as a solid material, soft or hard gel, liquid, spray, aerosol, roll-on formulation, pad-applied formulation, film-forming formulation, and a mask.

The wet method and hot processing method described above for the pharmaceutical compositions may be used to prepare the compositions containing cosmetic active ingredients by incorporating one or more of the cosmetic active ingredients and/or additive either prior to, contemporaneously with, and/or following the addition of the gelling adjuvant.

In still other embodiments, method and kits for preparing and delivering reversely thermo-reversible pharmaceutical and cosmetic compositions containing the water-soluble supramolecular complexes of the present invention for topical, mucosal, and/or oral applications may be provided comprising the steps of preparing and providing a pharmaceutical and cosmetic composition as a hydrogel or solution or a solid composition that is hydrated to form a hydrogel vehicle; and applying the hydrogel composition or solution to the mucous membranes. The hydrogel composition or solution may be applied to the topical and/or mucosal target, in an amount sufficient to deliver a non-toxic, pharmacologically effective amount of the pharmaceutical medicament and/or cosmetic active ingredient to the intended site of treatment and/or care/beauty for a controlled or sustained release of a variety of pharmaceutical medicaments and/or cosmetic active ingredients.

Exemplary cosmetic and personal care applications, for which the compositions may be used include, but are not limited to, baby products, such as baby shampoos, lotions, and creams; bath preparations, such as bath oils, tablet and salts, bubble baths, bath fragrances and bath capsules; eye makeup preparations, such as eyebrow pencil, eyeliner, eye shadow, eye lotion, eye makeup remover and mascara; fragrance preparations, such as colognes and toilet waters, powders and sachets; noncoloring hair preparations, such as hair conditioner, hair spray, hair straighteners, permanent waves, rinses shampoos, tonics, dressings and other grooming aids; color cosmetics; hair coloring preparations such as hair dye, hair tints, hair shampoos, hair color sprays, hair lighteners and hair bleaches; makeup preparations such as foundations, powders, leg and body paints, lipstick, makeup bases, rouges and makeup fixatives; oral hygiene products such as dentifrices and mouthwashes; personal cleanliness, such as bath soaps and detergents, deodorants, douches and feminine hygiene product; shaving preparations such as aftershave lotion, beard softeners, shaving soap and pre-shave lotions; skin care preparations such as cleansing preparations, skin antiseptics, depilatories, face and neck cleansers, body and hand cleansers, moisturizers, skin fresheners; and suntan preparations such as suntan creams, gels and lotions, indoor tanning preparations.

Preparation of the above-named cosmetic compositions and others may be accomplished with reference to any of the cosmetic formulation guidebooks and industry journals which are available in the cosmetic industry. These references supply standard formulations which may be modified by the addition or substitution of the water-soluble supramolecular complexes of the present invention into the formulation. Suitable guidebooks include Cosmetics and Toiletries Magazine, Vol. 111 (March, 1996); Formulary: Ideas for Personal Care; Croda, Inc, Parsippany, N.J. (1993); and Cosmeticon: Cosmetic Formulary, BASF, which are hereby incorporated in their entirety by reference. The cosmetic composition may be in any form. Suitable forms include but are not limited to solid doses, liquids, gels, lotions, creams, hard gel sticks, roll-ons formulations, mousses, aerosol sprays, pad-applied formulations, and film-forming formulations.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention.

EXAMPLES

The following non-limiting examples are offered as being illustrative of the properties of exemplary compositions of the present invention. In the following example, concentrations are expressed in weight percent (wt. %), and deionized water is utilized to make the formulations. Unless otherwise specified, the formulation temperature is at room temperature at about 22° C.

A clear and transparent hydrogel having the composition of Table 1 was produced by the following wet processing method.

TABLE 1

Hydrogel contains 3% salicylic acid

| No. | Ingredients | Wt. % | Wt. (g) |
|---|---|---|---|
| 1 | Poloxamer 407 | 12.5 | 25.0 |
| 2 | De-ionized Water | 81.0 | 162.0 |
| 3 | Salicylic acid | 3.0 | 6.0 |
| 4 | Laureth-4 | 3.5 | 7.0 |

Poloxamer 407 was first dissolved in water while stirring at a temperature below 10° C. After forming a uniform homogenous solution, the solution temperature was raised to about 60° C. Salicylic acid was added while mixing at that temperature. After the salicylic acid was totally dissolved, laureth-4 was then added drop-wise to the solution while mixing at about 60° C. After cooling to room temperature, a clear and transparent gel was obtained.

The gel was then subjected to a hot air drying process to remove water. The obtained anhydrous material was a white waxy solid material at room temperature capable of dissolving in water to form clear and transparent gels or solutions depending on the concentration in water without forming any precipitation.

A white waxy solid having the composition of Table 2 was produced by the following hot melt processing method.

TABLE 2

Melt processing composition

| No. | Ingredients | Wt. % | Wt. (g) |
|---|---|---|---|
| 1 | Poloxamer 407 | 65.8 | 25.0 |
| 2 | De-ionized water | 0.00 | — |
| 3 | Salicylic acid | 15.8 | 6.0 |
| 4 | Laureth-4 | 18.4 | 7.0 |

The hot melt processing method included the following:

The Poloxamer 407 was first heated to about 55-120° C. while stirring. The salicylic acid was then added while stirring for about 60 minutes. Finally, the laureth-4 was added while stirring for about 60 minutes at the same temperature. After cooling composition, a white waxy solid was obtained.

No water was added to the hot melt processing method, therefore, the resulting wax-like product was anhydrous or at least a material having a low water content. It was found that the wax-like material obtained through the hot melt process could be re-dissolved in water to form a clear and transparent solution or gel depending on the concentration of the solution without any visible precipitation.

Two separate clear and transparent hydrogels having the composition of Table 3 were produced, one made according to the solution method and the other according to the hot melt processing method.

TABLE 3

Solution and Hot melt processing of delivery system

| | | Solution process | | Hot Melt process |
|---|---|---|---|---|
| No. | Ingredients | Wt. % | Wt. (g) | Wt. (g) |
| 1 | Poloxamer 407 | 12.5 | 25.0 | 25.0 |
| 2 | De-ionized water | 83.5 | 167.0 | — |
| 3 | Laureth-4 | 4.0 | 8.0 | 8.0 |

The solution process included the following:

Poloxamer 407 was first dissolved in water while stirring at a temperature below 10° C. After forming a homogenous solution, the solution was heated to about 60° C. The associative gelling adjuvant laureth-4 was then added to the polymer solution while stirring at a temperature of about 60° C. The obtained hydrogel had a sol-gel transition temperature at about 24° C.

The hot melt process included the following:

Poloxamer 407 was heated in a beaker at a temperature of about 55-120° C. for 40-60 minutes while stirring. Laureth-4 was then added at that temperature and stirred for an additional 60 minutes. After cooling to room temperature, a solid white wax-like material was obtained.

Approximately 2.04 g of the wax-like material was dissolved in about 10.3 g of water at 60-65° C. while stirring to produce a solution having the same Poloxamer 407 concentration as the hydrogel made according to the solution process. After complete dissolution, the mixture was allowed to cool to room temperature resulting in a hydrogel having a sol-gel transition temperature of about 24° C., the same as the solution processed hydrogel.

It was interestingly observed that the wax-like material made according to the hot melt processing method was easily dissolved in water while being heated and formed a clear and transparent solution or gel. The supramolecular complexes therefore differ from Poloxamer 407 by itself which is known to be more easily dissolved in cold water at temperatures below 20° C.

Two separate clear and transparent hydrogels comprising terbinafine hydrochloride and having the composition of Table 4 were produced, one according to the solution method and the other according to the hot melt processing method followed by dissolution in water.

TABLE 4

| | | Solution process | | Hot Melt process |
|---|---|---|---|---|
| No. | Ingredients | Wt. % | Wt. (g) | Wt. (g) |
| 1 | Poloxamer 407 | 12.5 | 25.0 | 25.0 |
| 2 | De-ionized water | 75.0 | 150.0 | — |
| 3 | Propylene glycol | 3.0 | 6.0 | 6.0 |
| 4 | PEG-400 | 3.0 | 6.0 | 6.0 |
| 5 | Salicylic acid | 2.0 | 4.0 | 4.0 |
| 6 | Menthol | 0.1 | 0.2 | 0.2 |
| 7 | Terbinafine hydrochloride | 1.0 | 2.0 | 2.0 |
| 8 | Laureth-4 | 3.4 | 6.8 | 6.8 |

Solution Process:

Poloxamer 407, water, propylene glycol, and PEG-400 were combined while stirring at a temperature below 10° C. to form a homogenous solution. The temperature was then raised to 55-60° C. and the salicylic acid was added while stirring until salicylic acid was completely dissolved. The terbinafine hydrochloride was added at 55-60° C. while stirring until it was dissolved. The menthol was then similarly added at 55-60° C. while stirring until complete dissolution. Finally, the laureth-4 was added at 55-60° C. while stirring until a clear and transparent solution was obtained. The solution was allowed to cool down to room temperature resulting in a transparent gel.

Hot Melt Process:

A mixture of Poloxamer 407, propylene glycol, and PEG-400 was mixed in a beaker at about 55-120° C. for 60 minutes while stirring. The salicylic acid was then added while maintaining the same temperature and stirring for 50 minutes. The terbinafine hydrochloride was then added at 55-120° C. and stirred for 50 minutes followed by addition of the menthol at 55-120° C. while maintaining stirring for about 10 minutes. Finally, laureth-4 was added at about 55-120° C. and stirred for 40 minutes. Upon cooling to room temperature, a white soft wax-like material was obtained.

The material obtained from the hot melt process was dissolved in water when heated at about 55-60° C. while stirring to obtain a clear and transparent hydrogel, similar to the solution processed hydrogel. It was observed that the solution process and hot melt process resulted in hydrogels with the same characteristics; therefore, the supramolecular complexes are likely formed by either method.

The results and observations from the above examples suggest that the supramolecular complexes containing active ingredients may be provided in anhydrous forms either by a hot melt process or after removing water from a solution or gel composition that includes the complexes. The anhydrous forms may be re-dissolved in water to form clear and transparent solutions or gels depending on the concentration of the solution. Therefore, the hydration and dehydration of the supramolecular complexes may be a fully reversible process.

The results further suggest that supramolecular complexes or self-assembly of inter-molecular complexes through non-covalent bonds are formed through supramolecular chemistry among the block copolymer (e.g. Poloxamer 407), associative gelling adjuvant (e.g. laureth-4) and active ingredient (e.g. salicylic acid). The complexes may be provided in an anhydrous form ranging from a soft wax-like material or paste to a hard wax-like material, and again may be easily re-dissolved in water to form clear and transparent solutions or gels.

What is claimed is:

1. A supramolecular complex comprising:
   (a) a water soluble block copolymer comprising at least two blocks of polyethylene oxide and at least one block of polypropylene oxide, and
   (b) at least one associative gelling adjuvant having a water solubility less than 0.5 g/100 ml at 20° C.;
   wherein the complex is soluble in water and has a softening point ranging from 10 to 60° C.;
   wherein the water soluble block copolymer is a triblock copolymer having the general formula of HO-$(EO)_a(PO)_b(EO)_a$-H, wherein $(EO)_a$ are the polyethylene oxide blocks, $(PO)_b$ is the polypropylene oxide block, a is in the range of about 50 to about 150 and b is in the range of about 35 to about 70;
   wherein the complex forms a clear and transparent gel after hydration.

2. The complex of claim 1, wherein a is about 101, and b is about 56.

3. The complex of claim 1, wherein a is about 141, and b is about 44.

4. The complex of claim 1, wherein the at least one associative gelling adjuvant is selected from the group consisting of oxyalkylated fatty alcohol, esters of oxyalkylated fatty alcohol, oxyalkylated alkyl alcohol, esters of oxyalkylated alkyl alcohol, oxyalkylated alkylaryl alcohol, oxyalkylated sorbitan ester, oxyalkylated triglyceride, oxyalkylated glyceryl ester, esters of oxyalkylated sorbitol, and mixtures thereof.

5. The complex of claim 4, wherein the oxyalkylated fatty alcohol is selected from the group consisting of laureth-2, laureth-3, laureth-4, laureth-5, and laureth-6; oleth-2, oleth-5, and oleth-10.

6. The complex of claim 4, wherein the oxyalkylated alkyl alcohol is selected from the group consisting of C12-13 pareth-2, C12-13 pareth-3, C12-13 pareth-4, C12-13 pareth-5, and C12-13 pareth-6.

7. The complex of claim 4, wherein the esters of oxyalkylated fatty alcohol is selected from the group consisting of di-PPG-2 myreth-9 adipate, di-PPG-2 myreth-10 adipate, and di-PPG-2 myreth-11 adipate.

8. The complex of claim 1 having a weight ratio of the water soluble block copolymer to the at least one associative gelling adjuvant of 0.5:1 to 15:1.

9. A transparent aqueous solution comprising the complex of claim 1 dissolved in water.

10. A transparent reversely thermo-reversible hydrogel comprising the complex of claim 1, having an adjustable sol-gel transition temperature in the temperature range of 4-45° C.

11. A composition comprising the complex of claim 1 and further comprising an effective amount of at least one pharmaceutical medicament, diagnostic compound or cosmetic active ingredient.

12. The composition of claim 11, wherein the at least one pharmaceutical medicament, diagnostic compound or cosmetic active ingredient is selected from the group consisting of anti-bacterial substances, anti-histamines, decongestants, anti-inflammatories, miotics, anti-cholinergics, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites, anesthetics, anti-fungal agents, amoebacidal compounds, trichomonacidal agents, analgesics, anti-arthritics, anti-asthmatics, anti-coagulants, anti-convulsants, anti-depressants, anti-diabetics, anti-neoplastics, anti-psychotics, anti-hypertensive agents, muscle relaxants, proteins, peptides, acne treatment agents, lubricating agents, vitamins, amino acids, tooth whitening agents, depilatory agents, insect repellants, antioxidants, anti-inflammatory agents, and mixtures thereof.

13. The composition of claim 11, wherein the at least one pharmaceutical medicament, diagnostic compound or cosmetic active ingredient is presented at a concentration ranging from about 0.001% to about 70%, by weight of the total composition.

14. The composition of claim 11, further comprising one or more pharmaceutically or cosmetic acceptable excipients selected from the group consisting of binders, flavorings, film forming polymers, preservatives, colorants, salts and fragrances.

15. The composition of claim 11, wherein the pharmaceutical compositions take a form selected from the group consisting of tablets, powders, and paste.

16. A transparent aqueous solution comprising the composition of claim 11 dissolved in water.

17. A transparent reversely thermo-reversible hydrogel comprising the composition of claim 11, having an adjustable sol-gel transition temperature in the temperature range of 4-45° C.

18. A method of preparing the complex of claim 1, comprising the steps of:
(a) heating said water soluble block copolymer to a temperature of 55 to 120° C.,
(b) mixing the heated copolymer with at least one associative gelling adjuvant at a temperature of 55 to 120° C. to form a mixture, and
(c) cooling the mixture to provide an anhydrous form.

19. A method of preparing the complex of claim 1, comprising the steps of:
(a) dissolving said water soluble block copolymer in water at a temperature below 20° C.,
(b) mixing the dissolved copolymer with at least one associative gelling adjuvant at a suitable temperature to form a transparent hydrogel or solution, and
(c) drying the transparent hydrogel or solution to remove water to provide an anhydrous form.

20. A supramolecular complex consisting of:
(a) a water soluble block copolymer comprising at least two blocks of polyethylene oxide and at least one block of polypropylene oxide, and
(b) at least one associative gelling adjuvant having a water solubility less than 0.5 g/100 ml at 20° C.;
wherein the complex is soluble in water and has a softening point ranging from 10 to 60° C.;
wherein the water soluble block copolymer is a tri-block copolymer having the general formula of HO-$(EO)_a(PO)_b(EO)_a$-H, wherein $(EO)_a$ are the polyethylene oxide blocks, $(PO)_b$ is the polypropylene oxide block, a is in the range of about 50 to about 150 and b is in the range of about 35 to about 70;
wherein the complex forms a clear and transparent gel after hydration.

21. A composition comprising the complex of claim 20 and an effective amount of at least one pharmaceutical medicament, diagnostic compound or cosmetic active ingredient.

22. The composition of claim 21, wherein the at least one pharmaceutical medicament, diagnostic compound or cosmetic active ingredient is selected from the group consisting of anti-bacterial substances, anti-histamines, decongestants, anti-inflammatories, miotics, anti-cholinergics, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites, anesthetics, anti-fungal agents, amoebacidal compounds, trichomonacidal agents, analgesics, anti-arthritics, anti-asthmatics, anti-coagulants, anti-convulsants, anti-depressants, anti-diabetics, anti-neoplastics, anti-psychotics, anti-hypertensive agents, muscle relaxants, proteins, peptides, acne treatment agents, lubricating agents, vitamins, amino acids, tooth whitening agents, depilatory agents, insect repellants, antioxidants, anti-inflammatory agents, and mixtures thereof.

23. The composition of claim 21, wherein the at least one pharmaceutical medicament, diagnostic compound or cosmetic active ingredient is presented at a concentration ranging from about 0.001% to about 70% by weight of the total composition.

24. The composition of claim 21, further comprising one or more pharmaceutically or cosmetic acceptable excipients selected from the group consisting of binders, flavorings, film forming polymers, preservatives, colorants, salts and fragrances.

25. The composition of claim 21, wherein the pharmaceutical compositions take a form selected from the group consisting of tablets, powders, and paste.

* * * * *